United States Patent [19]

Miyamoto et al.

[11] Patent Number: 4,560,788

[45] Date of Patent: Dec. 24, 1985

[54] PROCESS FOR PRODUCING OLIGOESTERS

[75] Inventors: Akira Miyamoto; Senzo Shimizu; Masayoshi Okamura; Hiroka Tanisake; Yasumitsu Higuchi; Toshio Hidaka; Koji Yamamoto; Toshiyuki Abe, all of Kanagawa, Japan

[73] Assignee: Mitsubishi Gas Chemical Company, Inc., Tokyo, Japan

[21] Appl. No.: 520,763

[22] Filed: Aug. 8, 1983

Related U.S. Application Data

[63] Continuation of Ser. No. 323,500, Nov. 20, 1981, abandoned.

[30] Foreign Application Priority Data

Nov. 22, 1980 [JP] Japan .................... 55-165158

[51] Int. Cl.$^4$ .................................. C07C 67/26
[52] U.S. Cl. .............................. 560/91; 528/297; 560/93; 560/94
[58] Field of Search ................. 560/91, 93, 94; 528/297

[56] References Cited

U.S. PATENT DOCUMENTS 4,306,056  12/1981  Miyamoto et al. .............. 528/297

Primary Examiner—James H. Reamer
Assistant Examiner—Vera C. Clarke
Attorney, Agent, or Firm—Fleit, Jacobson, Cohn & Price

[57] ABSTRACT

A process for producing an oligoester which comprises:
(a) the step of reacting isophthalic acid and propylene oxide in a reaction medium in the presence of a specific catalyst comprising a tetraalkyl ammonium compound to prepare an oligoester, and
(b) the step of removing volatile components from the resulting oligoester by heating the oligoester at a temperature of 180°–280° C. is disclosed. The oligoester is used as an intermediate for preparing unsaturated polyesters.

2 Claims, No Drawings

PROCESS FOR PRODUCING OLIGOESTERS

This application is a continuation of application Ser. No. 323,500, filed Nov. 20, 1981, now abandoned.

BACKGROUND OF THE INVENTION

This invention relates to process for producing oligoesters, which are useful as an intermediate for preparing unsaturated polyesters, from isophthalic acid and propylene oxide.

In the present specification "unsaturated polyester" indicates the polyester which is prepared from dicarboxylic acid components containing unsaturated dicarboxylic acid and polyol components and is not yet mixed with a vinyl monomer as a crosslinking agent. The mixture of the unsaturated polyester and a vinyl monomer is referred to as "unsaturated polyester resin" in the present specification.

It is known that unsaturated polyester resins obtained by using isophthalic acid as a dicarboxylic acid component (sometimes hereinunder referred to as isophthalic acid type unsaturated polyester resin) are superior to unsaturated polyester resins obtained by using orthophthalic acid as a dicarboxylic acid component with respect to such properties as water resistance, chemical resistance and mechanical properties. However, the time required for esterification is longer when isophthalic acid is used as a dicarboxylic acid component than when orthophthalic acid is used.

The process for producing isophthalic acid type unsaturated polyesters are of two types; one stage process and two stage process. In the one stage process, all of the dicarboxylic acid components containing isophthalic acid and unsaturated dicarboxylic acid are reacted with all of the polyol components, such as a glycol or glycols, simultaneously. The two stage process comprises reacting isophthalic acid with at least one polyol component, such as a glycol or glycols, until the acid value of the product amounts to less than a definite value, for example less than 30, to form an oligoester which is a precursor for unsaturated polyester, followed by reacting unsaturated dicarboxylic acid or its anhydride with the resulting oligoester. Though the reaction time of the one stage process is shorter than that of the two stage process, it is known that unsaturated polyester resins produced by the one stage process are inferior to unsaturated polyester resins produced by the two stage process with respect to various properties.

It was known in the art that an addition product of an aromatic dicarboxylic acid and an alkylene oxide, namely an oligoester, can be produced by reacting the two components in the presence of an amine compound catalyst, such as a tertiary amine. However, when the oligoester obtained by the above process is utilized as an intermediate for unsaturated polyesters, the resulting polyesters are apt to be seriously discolored, and are limited to reproducibility of various characteristics with reference to the curing step of unsaturated polyester resins and various properties of the cured resins, such as mechanical properties, chemical resistance, water resistance and so on, and additionally they have poor storage stability. So the resins are not of practical use.

Reaction of an aromatic dicarboxylic acid with an alkylene oxide in the absence of any catalyst has been attempted to overcome the above-mentioned shortcoming. In this case the addition reaction between isophthalic acid and an alkylene oxide is hard to realize because of the high melting point of isophthalic acid and poor solubility of isophthalic acid in the reaction medium and simultaneously polymerization of the alkylene oxide itself occurs to form the oligoester having an ether bond to considerable extent. In addition, it takes much time to lower the acid value of the oligoester to the necessary extent. So, it has been believed to be impossible to economically obtain unsaturated polyester resins with suitable characteristics by reacting an aromatic dicarboxylic acid, especially isophthalic acid, with an alkylene oxide in the absence of any catalyst.

The inventors of the present invention have carried out intensive researches on oligoesters obtained by the addition reaction of isophthalic acid and an alkylene oxide, particularly propylene oxide. As a result, a process for producing oligoesters which comprises (a) the step of reacting isophthalic acid with propylene oxide in a reaction medium in the presence of an amine compound catalyst to produce an oligoester, (b) the step of removing volatile components from the oligoester obtained in step (a) by heating the oligoester at the temperature within the range of 180°–300° C. and (c) the step of treating the oligoester obtained in the step (b) with a silica-alumina compound having absorbing property, has been proposed, as exemplified in U.S. Ser. No. 150,691 filed on May 16, 1980 by Miyamoto et al., now U.S. Pat. No. 4,306,056.

SUMMARY OF THE INVENTION

One object of this invention is to provide a process for producing oligoesters obtained from isophthalic acid and propylene oxide by a more simple operation without a step of treating the oligoester with an absorbent than the operation claimed in U.S. Ser. No. 150,691 above, now U.S. Pat. No. 4,306,056.

The other object of this invention is to provide a process for economically producing within a short time oligoesters which are useful as a precursor for unsaturated polyester resins having excellent water resistance, chemical resistance and mechanical properties.

This invention relates to process for producing an oligoester which comprises:

(a) the step of reacting 1 mol of isophthalic acid with 1.1–3.3 moles of propylene oxide in a reaction medium, which is a reaction product of isophthalic acid with propylene oxide and/or propylene glycol, in the presence of a tetraalkyl ammonium compound as a catalyst to prepare an oligoester and (b) the step of removing volatile components from the oligoester obtained in step (a) by heating the oligoester at a temperature of 180°–280° C.

DETAILED DESCRIPTION OF THE INVENTION

The first step of this invention relates to addition reaction of isophthalic acid with propylene oxide. The addition reaction may be carried out by adding isophthalic acid to an oligoester as a reaction medium in the presence of a tetraalkyl ammonium compound as a catalyst, followed by continuously introducing propylene oxide into the mixture with stirring at atmospheric pressure or under pressure while heating the mixture at a definite temperature. It is necessary to employ from 1.1 to 3.3 moles of propylene oxide, preferably 1.2 to 3.0 moles of propylene oxide, for one mole of isophthalic acid. In this addition reaction, other saturated dicarboxylic acids may be added to the reaction system in place of a part of isophthalic acid. Examples of the saturated dicarboxylic acids to be used herein include ortho-phthalic acid, phthalic anhydride, terephthalic acid, tetrahydrophthalic acid, 3,6-endomethylene tetrahydrophthalic acid, pimelic acid, adipic acid, glutaric acid, succinic acid and sebacic acid. The other saturated dicarboxylic acid may be used in an amount of less than 30 mol percent of isophthalic acid used. Other alkylene oxides may be also used in place of a part of propylene oxide. Examples of the other alkylene oxides include ethylene oxide, butylene oxide, amylene oxide and hexene oxide. The other alkylene oxides may be used in an amount of less than 30 mol percent of propylene oxide used.

In the first step of this invention, one object of using a tetraalkyl ammonium compound as a catalyst is to promote the reaction of isophthalic acid and propylene oxide and another object thereof is to provide oligoesters with a desired structure.

The tetraalkyl ammonium compounds used as a catalyst in the first step of this invention include tetraalkyl ammonium hydroxides represented by general formula (I)

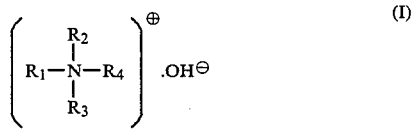

and tetraalkyl ammonium salts represented by general formula (II)

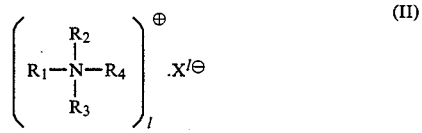

in formulas (I) and (II), $R_1$, $R_2$, $R_3$ and $R_4$ may be the same or different and independently are alkyl group having 1–4 carbon atoms or hydroxy-substituted alkyl group having 1–4 carbon atoms and X is a halogen atom, such as chlorine, bromine and iodine; a residue of carbonic acid or bicarbonic acid; a residue of an aliphatic mono- or di-carboxylic acid having 1 to 10 carbon atoms, such as acetic acid, propionic acid, butyric acid, oxalic acid and succinic acid; and a residue of an aromatic mono- or di-carboxylic acid or an aromatic mono- or di-carboxylic acid which is nuclear-substituted with one or more alkyl having 1–3 carbon atoms, such as benzoic acid, toluic acid, ortho-phthalic acid, terephthalic acid and isophthalic acid, and in formula (II), l is an integer of 1 or 2.

Examples of the tetraalkyl ammonium compounds include tetramethyl ammonium chloride, bromide, iodide, hydroxide, bicarbonate, carbonate or benzoate; tetraethyl ammonium chloride, bromide, iodide, hydroxide, bicarbonate, carbonate or benzoate; tetrapropyl ammonium chloride, bromide or hydroxide; tetrabutyl ammonium chloride or bromide; bis(tetramethyl ammonium)phthalate, isophthalate or terephthalate; bis(tetraethyl ammonium)phthalate, isophthalate or terephthalate; bis(2-hydroxyethyltriethyl ammonium) isophthalate; bis(2-hydroxyethyltripropyl ammonium) isophthalate; mono(2-hydroxypropyltriethyl ammonium)isophthalate; and bis(tetraethylammonium)oxalate. The tetraalkyl ammonium compound can be used alone or mixture thereof.

The addition reaction proceeds as shown in the following:

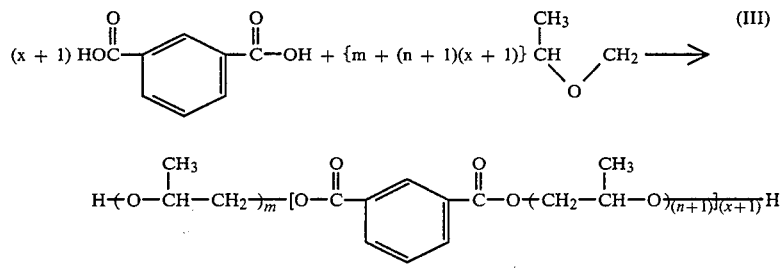

wherein n, m and x are independently 0 or integer of 1,2,3 . . . .

The larger is the amount of the tetraalkyl ammonium compound as a catalyst, the greater is the proportion of the oligoester of formula (III) in which n and m are each a relatively small integer in the resulting product. In other words, the larger is the amount of tetraalkyl ammonium compound as a catalyst, the lower is the proportion of ether bond in the resulting oligoester.

On the other hand, when the catalyst is used in a smaller amount, propylene oxide is apt to react with the terminal hydroxyl group of the resulting oligoester to form ether bonds in the oligoester. As a result, a part of propylene oxide is hard to participate in decreasing the acid value of the resulting oligoester. (In this case, decrease in the acid value of the resulting oligoester is achieved by supplying additional propylene oxide into the reaction system or by increasing the degree of condensation of the resulting oligoester.)

Thus, there has been found the fact that when oligoesters are produced from isophthalic acid and propylene oxide according to the process of the present invention, the proportion of ether bond in the oligoesters can be controlled by changing the amount of a catalyst to be used. The fact gives rise to the same result as in the process which comprises using dipropylene glycol or tripropylene glycol in place of a part of propylene glycol in the conventional esterification process for producing unsaturated polyesters. This means that unsaturated polyester resin having desired characteristics can be easily produced from the same raw materials by changing the production conditions. Therefore, according to the present invention the properties of unsaturated polyester resins are easily controlled. This is one of the significant features of this invention. As the proportion of ether bond in an oligoester increases, modulus and heat distortion temperature of the cured unsaturated polyester resin produced from the oligoester lowers and flexibility of the cured resin is improved.

The proportion of ether bond in an oligoester is quantitatively determined by ASTM D 2998-71.

Considering the properties of unsaturated polyester resins to be prepared, the amount of the catalyst to be employed is in the range of 0.001-1.5% by weight on the basis of isophthalic acid.

As mentioned above, the properties of the oligoester depend on the amount of the catalyst used. In addition, the properties of the oligoester also depend on molar ratio of propylene oxide to isophthalic acid employed. As the molar ratio decreases, the viscosity of the oligoester is increased until it becomes solid.

In order to obtain the oligoester having a low acid value, it is necessary to increase the degree of condensation of the oligoester.

The production of oligoesters, namely the addition reaction, is carried out at atmospheric pressure or under pressure within a temperature range of 100°-230° C., preferably 110°-220° C. When the reaction is carried out under pressure, the pressure depends on reaction conditions, such as rate of propylene oxide feed, kind and amount of solvents employed, amount of catalyst employed and reaction temperature. In general, the pressure may be less than 15 Kg/cm$^2$G. The reaction time depends on the above reaction conditions and may be in the range of 10-240 minutes, preferably 15-180 minutes. One of the advantages of the present invention is that oligoesters can be produced within a short time.

The same oligoester which is the object product of this invention can be used as a reaction medium. Oligoesters having similar structure, such as oligomers obtained by conventional esterification of isophthalic acid and propylene glycol can be used as the reaction medium.

The second step of this invention comprises heating the reaction product obtained in the above first step to remove volatile components from the reaction system such as unreacted alkylene oxide, catalyst and all other compounds formed by decomposition through the thermal treatment. To remove the volatile components, the reaction mixture is heated at 180°-280° C., preferably 220°-270° C. at atmospheric pressure. If desired, it may be practiced under reduced pressure. When the acid value of the oligoester obtained by the first step does not lower sufficiently, esterification reaction proceeds during the heating step, whereby water evolved is removed and the acid value of the oligoester lowers rapidly. According to the second step, useful properties can be imparted to the oligoester in the aim of preparing unsaturated polyester resin with good characteristics.

As another embodiment in the second step of the present invention, a glycol or glycols may be added to the reaction product containing the oligoester obtained in the first step before carrying out the second step. In this case, the acid value of the oligoester also lowers rapidly. According to this embodiment, useful precursors for unsaturated polyesters can be prepared. Examples of the glycols include propylene glycol as well as ethylene glycol, diethylene glycol, dipropylene glycol, 1,3-butylene glycol and neopentyl glycol.

As still another embodiment in the second step of the present invention, isophthalic acid may be added to the reaction product of the first step before carrying out the second step. In this case, esterification reaction occurs during the heating step simultaneously, whereby the proportion of isophthalic acid component to propylene oxide component contained in the oligoester so treated can be changed. In general the proportion of isophthalic acid component to propylene oxide component contained in the oligoester depends on the proportion of isophthalic acid to propylene oxide employed in the first step. However, according to this embodiment, the proportion of isophthalic acid component to propylene oxide component contained in the oligoester can also be adjusted by the second step. This makes it possible to prepare unsaturated polyester resins having a variety of properties. That is, practically useful oligoesters of isophthalic acid and propylene oxide can be prepared according to this embodiment.

According to the present invention, oligoesters having a variety of characteristics which are useful as a precursor for unsaturated polyester resins can be produced within a short time by a simple operation. The oligoesters obtained by this process have from 0.02 to 0.5 of ether bond per one isophthalic acid component in the molecular structure, and the ratio of ether bond to isophthalic acid component can be varied by selecting the proper process conditions corresponding to the properties required of the unsaturated polyester resins.

The invention is further illustrated, but in no way limited by the following Examples. The percent and parts are by weight, unless otherwise specified.

REFERENCE EXAMPLE 1

Into a reactor equipped with agitator, partial reflux condenser, thermometer and pipe for introducing nitrogen gas were charged 1661 grs of isophthalic acid and 1522 grs of propylene glycol. The mixture was heated to 205° C. while introducing nitrogen gas into the mixture at speed of 400 ml/min. Water formed through condensation was distilled while refluxing propylene glycol by passing steam of 100° C. through the partial reflux condenser. After about 10 hours 2810 grs of oligoester having acid value of 10, Gardner Color Scale of 2 and viscosity of 3500 poise (25° C.) was obtained. The oligoester was referred to as oligoester A. Glycol content in the oligoester A was determined by ASTM D 2998-71. The analysis showed that the content of glycol component containing ether bonds was 0.7% by mol of the total glycol component.

EXAMPLE 2

Into an autoclave equipped with agitator, thermometer, pipes for introducing nitrogen and propylene oxide, and reflux condenser equipped with thermometer at its top were charged 1882 grs of oligoester A, 1661 grs of isophthalic acid and 13.9 grs of tetraethylammonium chloride. Air in the autoclave was completely replaced by nitrogen gas. The mixture was heated to 160° C. 1162 Grs of propylene oxide was continuously added over 130 minutes at stirring rate of 500 rpm while maintaining the temperature at 160° C. While introducing propylene oxide, all of unreacted propylene oxide was refluxed by passing cold water through the partial reflux condenser. After adding the propylene oxide, the reaction was continued at 160° C. for additional 10 minutes. 4625 Grs of the reaction product having acid value of 35 (mg KOH/gr) was obtained. Thereafter, the reaction product was heated to 250° C. while bubbling nitrogen gas into the product at speed of 400 ml/min. Water formed through condensation and the volatile components were distilled by passing steam of 100° C. through the partial reflux condenser. After 30 minutes the reaction product was cooled to 100° C. Then 248 grs of propylene glycol was added to the product with stirring to obtain 4785 grs of oligoester having acid value of 2.0, Gardner Color Scale of 1 and content of remaining catalyst of 18 ppm (value calculated as nitrogen). The oligoester was referred to as oligoester B.

The analysis showed that the content of glycol component containing ether bonds was 6.80% by mol of the total glycol component.

In comparison of the process of this example with the process of Reference Example 1. It is clear that oligoester having good properties can be produced within a shorter period according to the process of this example.

EXAMPLE 3

Into an autoclave made of stainless steel equipped with agitator, thermometer and pipes for introducing nitrogen and propylene oxide were charged 1882 grs of oligoester A, 1661 grs of isophthalic acid, and 9.71 grs of tetramethylammonium chloride. Air in the autoclave was completely replaced by nitrogen gas. The mixture was heated to 210° C. 1162 Grs of propylene oxide was continuously added under pressure over 40 minutes at stirring rate of 500 rpm while maintaining the temperature at 210° C. While introducing propylene oxide, the maximum pressure in the autoclave increased to 2.1 $Kg/cm^2G$. After adding the propylene oxide, the reaction was continued at 210° C. for additional 10 minutes. 4620 Grs of the reaction product having acid value of 35 (mg KOH/g) was obtained. 2833 Grs of the reaction product was charged into a reactor equipped with agitator, partial reflux condenser and pipe for introducing nitrogen gas, and was heated to 250° C. while bubbling nitrogen gas into the reaction mixture at rate of 400 ml/min, and while passing steam of 100° C. through the partial reflux condenser to distil the volatile components and water formed through condensation. After 30 minutes, the reaction product was cooled to 100° C. Then 153 grs of propylene glycol was added to the product with stirring to obtain 2986 grs of oligoester having acid value of 2.0, Gardner Color Scale of 1 and content of remaining catalyst of 19 ppm (value calculated as nitrogen). The analysis showed that the content of glycol component containing ether bonds was 7.0 mol%.

EXAMPLE 4

Into an autoclave equipped with agitator, thermometer, pipes for introducing nitrogen and propylene oxide, and reflux condenser equipped with thermometer at its top were charged 1727 grs of oligoester B, 1661 grs of isophthalic acid and 9.71 grs of tetraethylammonium bromide. Air in the autoclave was completely replaced by nitrogen gas. The mixture was heated to 170° C. 930 Grs of propylene oxide was continuously added over 120 minutes at stirring rate of 500 rpm while maintaining the temperature at 170° C. While introducing propylene oxide, all of unreacted propylene oxide was refluxed by passing cold water through the partial reflux condenser. After adding the propylene oxide, the reaction was continued at 160° C. for additional 10 minutes. 4241 Grs of the reaction product having acid value of 44 (mg KOH/gr) was obtained. 2689 Grs of the reaction product was charged into a reactor equipped with agitator, partial reflux condenser and pipe for introducing nitrogen gas, and was heated to 250° C. while bubbling nitrogen gas into the reaction mixture at rate of 400 ml/min, and while passing steam of 100° C. through the partial reflux condenser to distil the volatile components and water formed through condensation. After 30 minutes, the reaction product was cooled.

The viscous, liquid oligoester having acid value of 3.0 and content of remaining catalyst of 17 ppm (value calculated as nitrogen was obtained.)

EXAMPLE 5

Into an autoclave equipped with agitator, thermometer, pipes for introducing nitrogen and propylene oxide, and reflux condenser equipped with thermometer at its top were charged 1882 grs of oligoester A, 1661 grs of isophthalic acid and 5.6 grs of tetraethylammonium chloride. Air in the autoclave was completely replaced by nitrogen gas. The mixture was heated to 160° C. 1162 Grs of propylene oxide was continuously added over 195 minutes at stirring rate of 500 rpm while maintaining the temperature at 160° C. While introducing propylene oxide, all of unreacted propylene oxide was refluxed by passing cold water through the partial reflux condenser. After adding the propylene oxide, the reaction was continued at 160° C. for additional 20 minutes. 4625 Grs of the reaction product having acid value of 46.5 (mg KOH/gr) was obtained. Thereafter, the reaction product was heated to 250° C. while bubbling nitrogen gas into the product at speed of 400 ml/min. Water formed through condensation and the volatile components were distilled by passing steam of 100° C. through the partial reflux condenser. After 30 minutes the reaction product was cooled to 100° C. Then 248 grs of propylene glycol was added to the product with stirring to obtain 4785 grs of oligoester having acid value of 3.6, Gardner Color Scale of 1 and content of remaining catalyst of 12 ppm (value calculated as nitrogen).

The analysis showed that the content of glycol component containing ether bonds of the resulting oligoester was 11.0% by mol of the total glycol component.

EXAMPLE 6

Into an autoclave equipped with agitator, thermometer, pipes for introducing nitrogen and propylene oxide, and reflux condenser equipped with thermometer at its top were charged 1882 grs of oligoester B, 1661 grs of isophthalic acid and 9.2 grs of tetramethylammonium chloride. Air in the autoclave was completely replaced by nitrogen gas. The mixture was heated to 180° C. 1162 Grs of propylene oxide was continuously added over 125 minutes at stirring rate of 500 rpm while maintaining the temperature at 180° C. While introducing propylene oxide, all of unreacted propylene oxide was refluxed by passinag cold water through the partial reflux condenser. After adding the propylene oxide, the reaction was continued at 180° C. for additional 10 minutes. 4620 Grs of the liquid reaction product having acid value of 35 (mg KOH/gr) and Gardner Color Scale of 1 was obtained. 2834 Grs of the reaction product and 1107 grs of isophthalic acid were charged into a reactor equipped with agitator, partial reflux condenser and pipe for introducing nitrogen gas and was heated to 250° C. while bubbling nitrogen gas into the reaction mixture at rate of 400 ml/min, and while passing steam of 100° C. through the partial reflux condenser to distil the volatile components and water formed through condensation. After distilling them at 250° C. for 120 minutes, the reaction product was cooled to 150° C. The reaction product was transferred into pan made of stainless steel. The resulting product had acid value of 12.0 (mg KOH/g), contained trace of remaining catalyst and had ring and ball softening point of 75° C. The product, oligoester was light yellow, solid at room temperature and fragile.

EXAMPLE 7

Into an autoclave equipped with agitator, thermometer, pipes for introducing nitrogen and propylene oxide, and reflux condenser equipped with thermometer at its top were charged 1727 grs of oligoester A, 1661 grs of isophthalic acid and 12.7 grs of bis(tetramethylammonium)isophthalate. Air in the autoclave was completely replaced by nitrogen gas. The mixture was heated to 170° C. 1162 Grs of propylene oxide was continuously added over 120 minutes at stirring rate of 500 rpm while maintaining the temperature at 170° C. While introducing propylene oxide, all of unreacted propylene oxide was refluxed by passing cold water through the partial reflux condenser. After adding the propylene oxide, the reaction was continued at 165° C. for additional 15 minutes. 4480 Grs of the reaction product having acid value of 37 (mg KOH/gr) was obtained. 2800 Grs of the reaction product was charged into a reactor equipped with agitator, partial reflux condenser and pipe for introducing nitrogen gas, and was heated to 250° C. while bubbling nitrogen gas into the reaction mixture at rate of 400 ml/min, and while passing steam of 100° C. through the partial reflux condenser to distil the volatile components and water formed through condensation. After 30 minutes, the reaction product was cooled. The viscous, liquid oligoester having acid value of 2.5, content of remaining catalyst of 15 ppm (value calculated as nitrogen) was obtained.

EXAMPLE 8

Into an autoclave equipped with agitator, thermometer, pipes for introducing nitrogen and propylene oxide, and reflux condenser equipped with thermometer at its top were charged 1727 grs of oligoester A, 1661 grs of isophthalic acid and 11.0 grs of tetramethylammonium bicarbonate. Air in the autoclave was completely replaced by nitrogen gas. The mixture was heated to 170° C. 1162 Grs of propylene oxide was continuously added over 120 minutes at stirring rate of 500 rpm while maintaining the temperature at 170° C. While introducing propylene oxide, all of unreacted propylene oxide was refluxed by passing cold water through the partial reflux condenser. After adding the propylene oxide, the reaction was continued at 165° C. for additional 15 minutes. 4485 Grs of the reaction product having acid value of 38 (mg KOH/gr) was obtained. 2800 Grs of the reaction product was charged into a reactor equipped with agitator, partial reflux condenser and pipe for introducing nitrogen gas, and was heated to 250° C. while bubbling nitrogen gas into the reaction mixture at rate of 400 ml/min and while passing steam of 100° C. through the partial reflux condenser to distil the volatile components and water formd through condensation. After 30 minutes, the reaction product was cooled.

The viscous, liquid oligoester having acid value of 2.8 and content of remaining catalyst of 18 ppm (value calculated as nitrogen) was obtained.

What is claimed is:

1. A process for producing an oligoester consisting of:
    (a) reacting isophthalic acid with propylene oxide, in a molar ratio of 1.1–3.3 moles of propylene oxide per mole of isophthalic acid, in a reaction medium in the presence of catalyst, the reaction medium being a reaction product of isophthalic acid with propylene oxide, propylene glycol, or a mixture thereof, and wherein the catalyst is selected from the group consisting of compounds represented by formula (I):

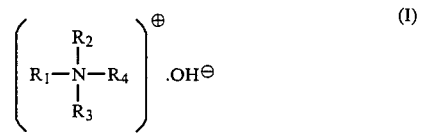

wherein $R_1$, $R_2$, $R_3$ and $R_4$ may be the same or different and are independently an alkyl group having 1 to 4 carbon atoms or a hydroxy-substituted alkyl group having 1 to 4 carbon atoms; compounds represented by the formula (II):

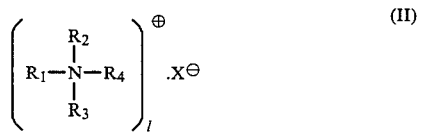

wherein $R_1$, $R_2$, $R_3$ and $R_4$ may be the same or different and are independently an alkyl group having 1 to 4 carbon atoms or a hydroxy-substituted alkyl group having 1 to 4 carbon atoms, $l$ is 1 or 2, and X is selected from the group consisting of halo, a carbonic acid or bicarbonic acid anion, an anion of an aliphatic mono- or di-carboxylic acid, an anion of an aromatic mono- or dicarboxylic acid, or an anion of an aromatic mono- or dicarboxylic acid which is nuclear-substituted with one or more alkyl groups having 1–2 carbon atoms; and mixtures thereof and (b) adding a glycol or glycols to the reaction product (a);
    (c) removing volatile components from the resulting oligoester by heating the oligoester to a temperature of about 180°–280° C.

2. A process for producing an oligoester consisting of:
    (a) reacting isophthalic acid with propylene oxide, in a molar ratio of 1.1–3.3 moles of propylene oxide per mole of isophthalic acid, in a reaction medium in the presence of catalyst, the reaction medium being a reaction product of isophthalic acid with propylene oxide, propylene glycol, or a mixture thereof, and wherein the catalyst is selected from the group consisting of compounds represented by formula (I):

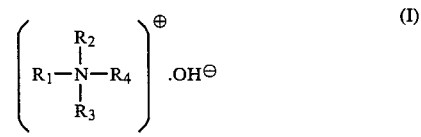

wherein $R_1$, $R_2$, $R_3$ and $R_4$ may be the same or different and are independently an alkyl group having 1 to 4 carbon atoms or a hydroxy-substituted alkyl group having 1 to 4 carbon atoms; compounds represented by the formula (II):

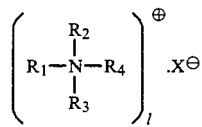

wherein $R_1$, $R_2$, $R_3$ and $R_4$ may be the same or different and are independently an alkyl group having 1 to 4 carbon atoms or a hydroxy-substituted alkyl group having 1 to 4 carbon atoms, $l$ is 1 or 2, and X is selected from the group consisting of halo, a carbonic acid or bicarbonic acid anion, an anion of an aliphatic mono- or di-carboxylic acid, an anion of an aromatic mono- or dicarboxylic acid, or an anion of an aromatic mono- or dicarboxylic acid which is nuclear-substituted with one or more alkyl groups having 1-2 carbon atoms; and mixtures thereof and (b) adding isophthalic acid to the reaction product of (a); and (c) removing volatile components from the resulting oligoester by heating the oligoester to a temperature of about 180°–280° C.

* * * * *